US011921104B2

United States Patent
Barry, Jr. et al.

(10) Patent No.: US 11,921,104 B2
(45) Date of Patent: Mar. 5, 2024

(54) CONTROL MATERIAL AND METHODS FOR CELL ANALYZERS

(71) Applicant: Medica Corporation, Bedford, MA (US)

(72) Inventors: Donald E. Barry, Jr., Groton, MA (US); Lindsay Goetz, Groton, MA (US)

(73) Assignee: Medica Corporation, Bedford, MA (US)

( * ) Notice: Subject to any disclaimer, the term of this patent is extended or adjusted under 35 U.S.C. 154(b) by 0 days.

(21) Appl. No.: 17/359,733

(22) Filed: Jun. 28, 2021

(65) Prior Publication Data

US 2022/0050095 A1    Feb. 17, 2022

Related U.S. Application Data

(63) Continuation of application No. 16/192,182, filed on Nov. 15, 2018, now Pat. No. 11,047,845.
(Continued)

(51) Int. Cl.
*G01N 33/49*    (2006.01)
*G01N 15/00*    (2006.01)
(Continued)

(52) U.S. Cl.
CPC .......... *G01N 33/49* (2013.01); *G01N 15/0227* (2013.01); *G01N 15/14* (2013.01);
(Continued)

(58) Field of Classification Search
CPC .............. G01N 15/14; G01N 15/1475; G01N 21/5907; G01N 33/49; G01N 33/5094; G01N 2015/008
(Continued)

(56) References Cited

U.S. PATENT DOCUMENTS 5,464,752 A * 11/1995 Kortright ......... G01N 33/56972
435/287.1
5,469,251 A * 11/1995 Kosaka .............. G01N 15/1475
356/336
(Continued)

FOREIGN PATENT DOCUMENTS

WO    WO-2012019118 A1 *  2/2012  ......... G01N 15/1475
WO    WO-2018009920 A1 *  1/2018  ............ B01L 3/5027

OTHER PUBLICATIONS

Bong-Hyun Jun., Multilayer fluorescene optically encoded beads for protein detection, Elsevier, 9, Mar. 2009, 3 pgs (Year: 2009).*
(Continued)

*Primary Examiner* — Stephanie E Bloss
*Assistant Examiner* — Kevin C Butler
(74) *Attorney, Agent, or Firm* — Kristofer E. Elbing

(57) ABSTRACT

This disclosure relates to verifying the operation of cell analyzers, including microscope-based cell imaging and counting analyzers. In one general aspect, a mixture of micro-beads having known characteristics is introduced into the analyzer. One or more images of the mixture are acquired with the analyzer's microscope, the images are analyzed, and a determination is made about whether results meet one or more predetermined quality control thresholds. Also disclosed is a hematology control material that can be used to perform the verification and includes a solvent, a dye dissolved in the solvent, and micro-beads suspended in the solvent. In another general aspect, a quality control method for the analyzers includes capturing images of samples that include patient cells using at least a microscope, extracting sample-specific information about properties of the patient samples from the images, and testing information from the samples against predetermined standards to verify the operation of the analyzer.

5 Claims, 15 Drawing Sheets

Related U.S. Application Data

(60) Provisional application No. 62/586,650, filed on Nov. 15, 2017.

(51) Int. Cl.

| | | |
|---|---|---|
| *G01N 15/02* | (2006.01) | |
| *G01N 15/14* | (2006.01) | |
| *G01N 21/59* | (2006.01) | |
| *G01N 21/64* | (2006.01) | |
| *G01N 33/50* | (2006.01) | |

(52) U.S. Cl.
CPC ..... *G01N 15/1475* (2013.01); *G01N 21/5907* (2013.01); *G01N 21/6458* (2013.01); *G01N 33/5094* (2013.01); *G01N 2015/008* (2013.01)

(58) Field of Classification Search
USPC .......................................................... 356/39
See application file for complete search history.

(56) References Cited

U.S. PATENT DOCUMENTS

| | | | | |
|---|---|---|---|---|
| 5,812,419 A | * | 9/1998 | Chupp | G01N 35/1004 702/20 |
| 5,939,326 A | * | 8/1999 | Chupp | G01N 35/1004 436/805 |
| 6,251,615 B1 | | 6/2001 | Oberhardt | G01N 15/1475 436/63 |
| 6,656,683 B1 | * | 12/2003 | Reuben | G01N 15/1475 435/325 |
| 7,312,085 B2 | * | 12/2007 | Chou | G01N 15/1468 422/50 |
| 7,553,453 B2 | * | 6/2009 | Gu | B01L 3/502776 436/63 |
| 7,764,821 B2 | * | 7/2010 | Coumans | C12M 41/36 382/128 |
| 8,339,586 B2 | * | 12/2012 | Zahniser | G01N 15/0227 382/133 |
| 8,383,043 B2 | * | 2/2013 | Padmanabhan | G01N 29/032 436/63 |
| 9,354,242 B2 | * | 5/2016 | Crowther | G01N 33/552 |
| 9,759,657 B2 | * | 9/2017 | Kiesel | G01N 21/6452 |
| 9,767,343 B1 | | 9/2017 | Jones | G01N 33/4915 |
| 10,267,722 B2 | * | 4/2019 | Rousseau | G01N 15/1434 |
| 11,047,845 B1 | * | 6/2021 | Barry, Jr. | G01N 33/49 |
| 2002/0028471 A1 | * | 3/2002 | Oberhardt | G01N 15/1475 382/133 |
| 2006/0094109 A1 | | 5/2006 | Trainer | G01N 35/0098 435/808 |
| 2007/0076190 A1 | * | 4/2007 | Nakaya | G01N 15/1475 382/134 |
| 2007/0190525 A1 | * | 8/2007 | Gu | G01N 33/5094 435/5 |
| 2008/0153170 A1 | * | 6/2008 | Garrett | G01N 33/80 436/63 |
| 2008/0254543 A1 | * | 10/2008 | Ryan | G01N 33/96 436/16 |
| 2010/0273168 A1 | * | 10/2010 | Krockenberger | G01N 15/1429 435/6.12 |
| 2012/0034647 A1 | * | 2/2012 | Herzog | G01N 21/6458 435/288.7 |
| 2014/0038230 A1 | * | 2/2014 | Beck | G01N 15/1463 435/39 |
| 2015/0219544 A1 | * | 8/2015 | Liu | G01N 1/4077 506/39 |
| 2016/0077091 A1 | * | 3/2016 | Tyrrell | G01N 33/94 422/403 |
| 2017/0328924 A1 | * | 11/2017 | Jones | G01N 1/312 |
| 2019/0339271 A1 | * | 11/2019 | Mohan | G02B 21/00 |
| 2020/0174241 A1 | * | 6/2020 | Jones | G01N 1/38 |
| 2021/0039093 A1 | * | 2/2021 | Jones | B01L 3/502715 |
| 2021/0231552 A1 | * | 7/2021 | Kim | G01N 15/147 |
| 2022/0050095 A1 | * | 2/2022 | Barry, Jr. | G01N 15/14 |

OTHER PUBLICATIONS

Ingrid Schmid, Flow Cytometry Recent Perspectives, Intech, www.intechopen.com, 13, Jun. 2012, pp. 11-203, 219, 385 (Year: 2012).*

Keisuke Goda, High-throughput single-microparticle imaging flow analyzer, Harvard University, Mar. 22, 2012, 6 pages (Year: 2012).*

Huang et al., "Development of a Flow Cytometry Based Miniature Chemical Fluid Analysis System Using Fluorescent Microbeads", SPIE Biomedical Optics, BIOS 97, conference proceedings, 1997, 9 pg(s) (Year: 1997).*

Natasha S. Barteneva et al, Imaging flow Cytometry: Coping with Heterogeneity in Biological Systems, Journal of Histochemistry & Cytochemistry, 2012, 11 pg(s) (Year: 2012).*

Christian K. Sieracki et al, An imaging-in-flow system for automated analysis of marine microplankton, Marine Ecology Prog Ser vol. 168: 285-296, Jul. 9, 1998 (Year: 1998).*

P. Schlenke et al., Evaluation of a Flow CYtometric Method for Simultaneous Leukocyte Phenotyping and Quantification by Fluorescent Microspheres, Wiley-Liss Inc., May 27, 1998, vol. 33:310-317 pgs (Year: 1998).*

Howard M. Shapiro, Personal CYtometers: Slow Flow or No Flow?, International Society for Analytical Cytology, Nov. 23, 2005, Cytometry Part A 69A:620-630 pgs (Year: 2005).*

Grossi et al., A Portable Sensor with Disposable Electrodes for Water Bacterial Quality Assessment, IEEE, Feb. 25, 2016, 9 pg(s) (Year: 2016).*

* cited by examiner

CONTROL MATERIAL AND METHODS FOR CELL ANALYZERS

CROSS-REFERENCE TO RELATED APPLICATIONS

This application claims priority to U.S. provisional application No. 62/586,650, which was filed on Nov. 15, 2017, and is herein incorporated by reference.

This application also relates to automated microscopic cell analysis and related technology described in U.S. published application number 20170328924, which was published on Nov. 16, 2017, and PCT published application number WO2018/009920, which was published on Jan. 11, 2018. Both of these applications are herein incorporated by reference.

FIELD OF THE INVENTION

This invention relates generally to Quality Control (QC) materials and calibrators and associated methods for microscopy-based and traditional cell imaging and counting systems.

BACKGROUND OF THE INVENTION

Complete Blood Count (CBC) control materials have been developed for cellular impedance and flow cytometry analyzers (traditional CBC systems). These traditional CBC systems generally consist of complex fluidic channels that require regular maintenance, calibration, and control accuracy. The risks of drifts and erroneous results are common due to clogs, partial blockages, and protein or salt buildup. A quality control material is therefore used to verify calibration, check for system failure, and demonstrate the proficiency of the operator. Traditional hematology control materials are made of stabilized blood from human and animal sources. The blood is stabilized by use of fixatives or preservatives so that it will not degrade to the point where cells can no longer be analyzed. This use of stabilized blood is a compromise to provide traditional CBC systems with a method of performing quality control on a regular basis.

Traditional CBC systems rely on the metaproperties of cells, such as DC conductivity, RF impedance, light scatter, and light extinction to count and classify cells. Counting and classifying cells based on these metaproperties has been determined empirically and validated through years of development and use of traditional CBC analyzers. It is through this use of metaproperties that stabilized control materials can simulate a fresh human blood sample. For example, avian red blood cells (RBC) can be used to simulate human lymphocytes. Under a microscope, the cells are clearly nucleated RBCs, but because the metaproperties are similar to those of human lymphocytes, the avian cells can be used as a surrogate. Preservatives and stabilizing agents are added to the blood to mitigate degradation of the cells in their natural matrix.

Often the metaproperties of stabilized blood controls do not exactly match those of fresh, human whole blood. The stabilization process can result in a significant alteration of size, shape, and granularity of the cells. For this reason, the software gate parameters used for counting and classifying controls on traditional CBC systems are generally different than those used for whole blood. These specialized gate parameters adjust for shifts between fresh human blood and stabilized blood control materials. In most cases, if one was to run a control material in blood sample mode, the results would not align with the provided insert ranges. Conversely, if a fresh blood is run in control mode, the results would also be erroneous.

Stabilized blood controls generally require special handling and storage and have a short shelf life. They generally are shipped and stored at refrigerated temperatures (2-8° C.) and are shipped overnight to ensure safe delivery. Once the control has been first used, it starts to degrade and can typically only be used for 1-2 weeks (open-container stability). Due to the short closed-container shelf life of typically less than 90 days, it is common for control manufacturers to require that laboratories issue standing orders to ensure that they can supply sufficient material to their customers. If a laboratory is not using a standing order or if it has used more than it has planned, it can be difficult and sometimes impossible to obtain control materials due to production schedule. These requirements can put a strain on laboratories and clinics that are not able to keep up with strict planning requirements. Also, these controls are expensive when compared to those for other common clinical diagnostic tests, such as clinical chemistry, blood gas, and electrolytes.

DETAILED DESCRIPTION OF ILLUSTRATIVE EMBODIMENTS

In one general aspect, the invention features a method of verifying the operation of a microscope-based cell imaging and counting analyzer. The method includes providing a mixture of micro-beads having known characteristics, introducing the mixture into the analyzer, acquiring one or more images of the mixture with the analyzer's microscope, analyzing the mixture of micro-beads in the images, and determining whether results of the analyzing meet one or more predetermined quality control thresholds.

In preferred embodiments, the mixture of beads can have a known concentration. The mixture of beads can be counted by image processing logic associated with the analyzer. The mixture of beads can be classified by image processing logic associated with the analyzer according to their different characteristics. The introducing the mixture can include introducing the mixture into a test cartridge and introducing the test cartridge into the analyzer. The providing can provide a mixture of micro-beads that includes at least some fluorescent micro-beads. The providing can provide a mixture of micro-beads of different sizes. The determining can include determining a distribution of bead sizes. The determining can include determining whether a micro-bead count meets a predetermined accuracy standard. The micro-bead count can be used for calibration of the system. The mixture can be stained and the method can further include determining whether the analyzer can detect the one or more properties of the stain within one or more predetermined quality control thresholds. The method can further include performing internal checks on patient samples.

In another general aspect, the invention features a microscope-based cell imaging and counting analyzer. The analyzer includes a microscope operative to acquire one or more images of a mixture of micro-beads, image processing logic responsive to the microscope and operative to analyze image characteristics of the mixture of micro-beads in the images, and quality control decision logic responsive to the image processing logic and operative to determine whether the image characteristics of the images of the micro-beads meet one or more predetermined quality control thresholds.

In a further general aspect, the invention features a hematology control material that includes a solvent, a dye dissolved in the solvent, and micro-beads suspended in the solvent. In preferred embodiments the micro-beads can include different sizes of micro-beads. The micro-beads can include at least some fluorescent micro-beads. At least some of the beads can be on the order of the size of at least one type of blood cells. At least some of the beads can be chosen to simulate platelets, red blood cells, white blood cells, and/or reticulocytes. At least some of the beads can be about in the range of 1-20 micrometers in diameter. The beads can be made of silica or polystyrene. The beads can be of different colors and/or shapes. The beads can be used to simulate a white cell differential. The beads can be in a concentration similar to human blood cells. The dye can simulate the absorbance of hemoglobin concentration of blood at a minimum of one wavelength of light. The beads can be in a concentration similar to abnormal human blood cell concentrations. The material can include a plurality of lots of beads each with bead concentrations at different levels to simulate normal and abnormal human blood cell concentrations.

In another general aspect, the invention features a quality control method for a microscopy-based cell imaging and counting analyzer. The method includes capturing images of samples that include patient cells using at least a microscope, extracting sample-specific information about properties of the patient samples from the captured images, and testing information from the samples against predetermined standards to verify the operation of the analyzer.

In preferred embodiments the testing can test information from the patient sample images captured by the microscope. The testing can include monitoring mean fluorescent intensity of cells by comparing the value to a pre-determined acceptable level. The testing can include comparing red blood cells in the images to a pre-determined set of features to verify that the red blood cells have been properly sphered. The testing can include comparing red blood cells in the images to a pre-determined roundness standard to verify that the red blood cells have been properly sphered. The testing can include comparing red blood cells in the images to a pre-determined secondary ring standard to verify that the red blood cells have been properly sphered. The testing can include using image processing to check for clots and microbubbles. The testing can include checking that the cells are not overlapping. The method can further include rejecting a sample and notifying a user based on invalid results of the step of testing. The capturing of patient sample images can be performed by a microscope and further including capturing further images of the patient samples with one or more additional cameras. The testing can use at least one macroscopic view camera to verify that an imaging region used for analysis is free from bubbles or voids. The testing can use at least one macroscopic view camera to calculate the area occupied by bubbles or voids in the imaging region that is used for analysis. The testing can use at least one macroscopic view camera to determine concentration gradients throughout the imaging region. The testing can use at least one macroscopic view camera to verify sample processing steps for diluting and mixing the patient sample with a diluent have been performed without error.

Materials and methods according to the invention can provide better solutions for quality control for microscopy-based cell imaging and counting systems, which can use different characteristics of cells than traditional CBC systems for counting and classification.

Benefits of materials according to the invention can include:
Improved operator and system control for microscopy-based cell imaging systems as compared to traditional CBC QC materials
Specific design for use with a microscopy-based cell imaging systems
Extensive procedural and system controls for every test
No need for cold-chain (2-8° C.) shipping or refrigerated storage
Longer shelf-life as compared to traditional CBC QC materials
Lower costs than traditional CBC QC materials

DETAILED DESCRIPTION OF AN ILLUSTRATIVE EMBODIMENT

I. Analyzer Structure and Operation

Figure 1:
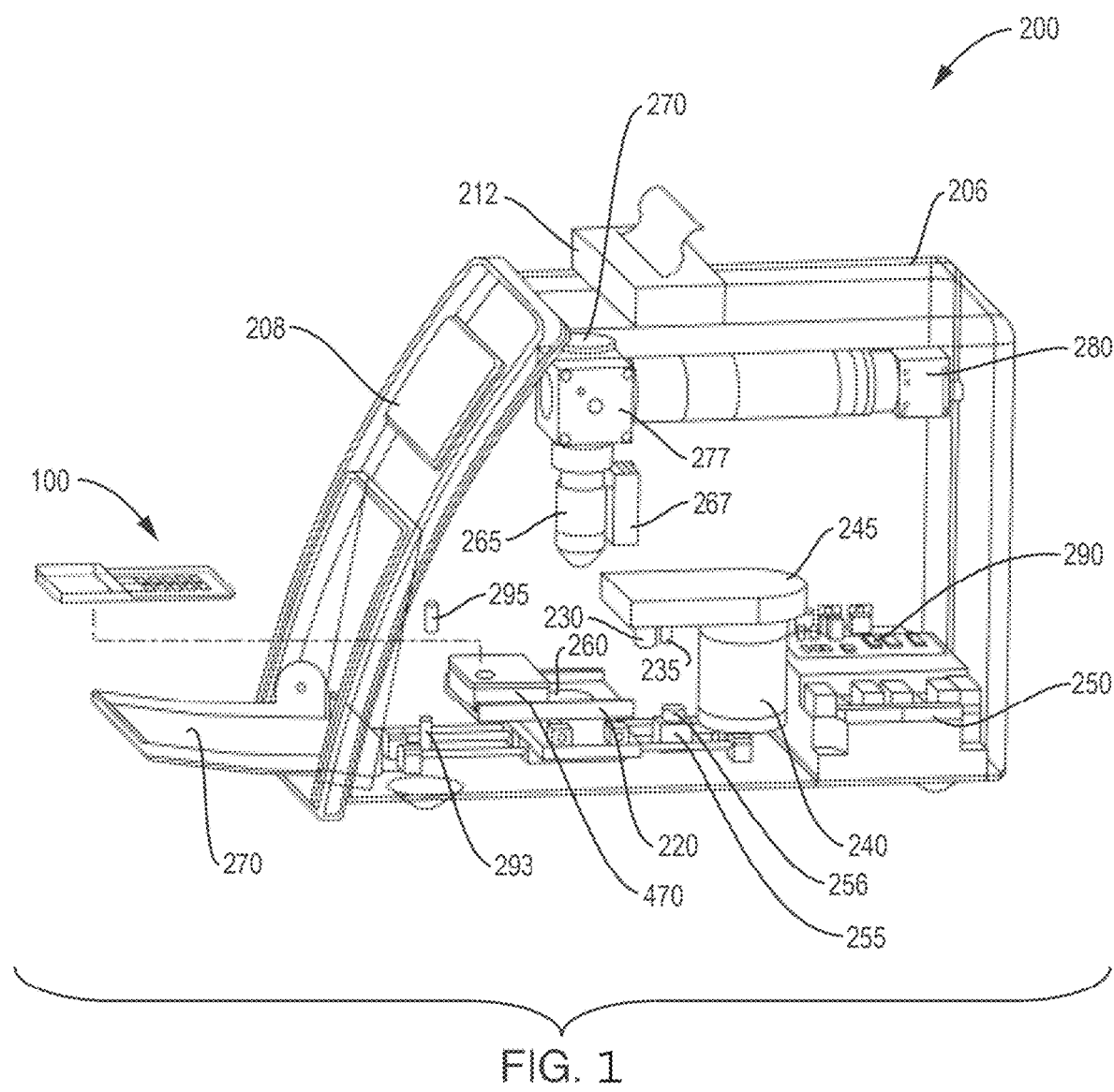
FIG. 1 is a cut-away view of an illustrative cell analyzer showing internal components with a test cartridge being inserted.

FIG. 1 is a cut-away view of an illustrative cell analyzer 200 with test cartridge 100 positioned so that the operator can introduce it into the analyzer. The structure and operation of this analyzer are discussed in more detail in the above-referenced published applications. From the outside of the cell analyzer 200, one can see the housing 206, a user-interface screen 208, a printer 212, and a cartridge loading door 270. When the cartridge loading door 270 is opened, the test cartridge 100 can be placed on a cradle 220 of x-y stage, configured to receive test cartridge 100 from the user. The cradle 220 provides mechanical alignment of the cartridge to facilitate connections that are made between the analyzer and the cartridge. For example, a mechanical presser foot 230 may be placed in contact with a flexible surface on the test cartridge to provide mechanical pressure onto packaged, on-board reagents.

A valve driver 235 can be positioned to operate a rotary valve on the test cartridge. A vacuum/pressure pump 240 supplies negative or positive pressure to a manifold 245, which interfaces with the test cartridge 100 when it is placed in the cell analyzer as described below. The cell analyzer 200 further includes system controller 250 to control movement of the fluids in the test cartridge by activating the vacuum/pressure pump 240, moving the mechanical presser foot 230, or operating the valve driver 235 according to pre-programmed sequences. A monitoring camera 255, positioned to acquire digital images of the fluids in the cartridge, provides feedback for the system controller 250. A monitoring light source 256 may be a ring illuminator that surrounds the lens of the monitoring camera 255. Information from the monitoring camera 255 is used to provide feedback for controlling movement of liquids, for positioning the rotary valve, and for confirming critical steps, as discussed in more detail below.

In this embodiment, a single monitoring camera is provided in a position below the test cartridge, but one or more additional monitoring cameras can also be used. In another embodiment, for example, two monitoring cameras are included in the cell analyzer, with one positioned below the test cartridge position facing upward, and another positioned above test cartridge facing downward. These are both provided with lower magnification than the analyzer's microscope so they can monitor larger areas.

Also shown in FIG. 1 are the components that comprise the automated microscope of the cell analyzer 200. At the base of the analyzer, bright-field light source 260 provides illumination through the test cartridge to the objective lens 265, operatively coupled to focusing mechanism 267. At the top of the analyzer, fluorescent light source 270 provides illumination through dichroic mirror 277 to provide fluorescent excitation of the sample. At the rear of the analyzer, digital camera 280 captures images of the cells in the test cartridge 100 and transmits them to image processor/computer 290. In some embodiments, the cell analyzer may further include a photometric light source 293 and photometric detector 295 for measuring light transmission at one or multiple wavelengths in a chamber in test cartridge 100, such as for measuring hemoglobin, as is more fully explained below.

Figure 2:
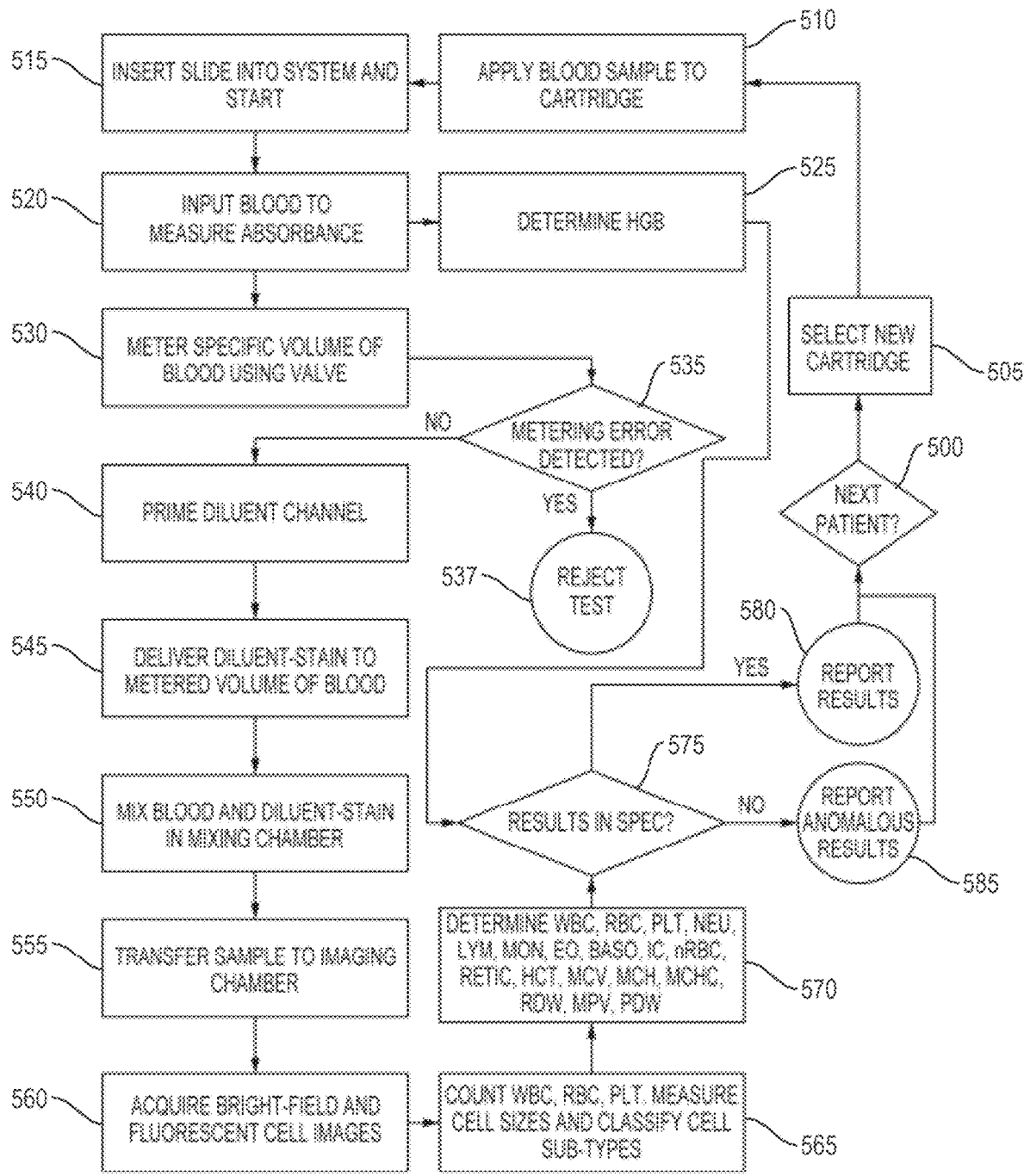
FIG. 2 is a flowchart illustrating the operation of the cell analyzer of FIG. 1.
Figure 8A:
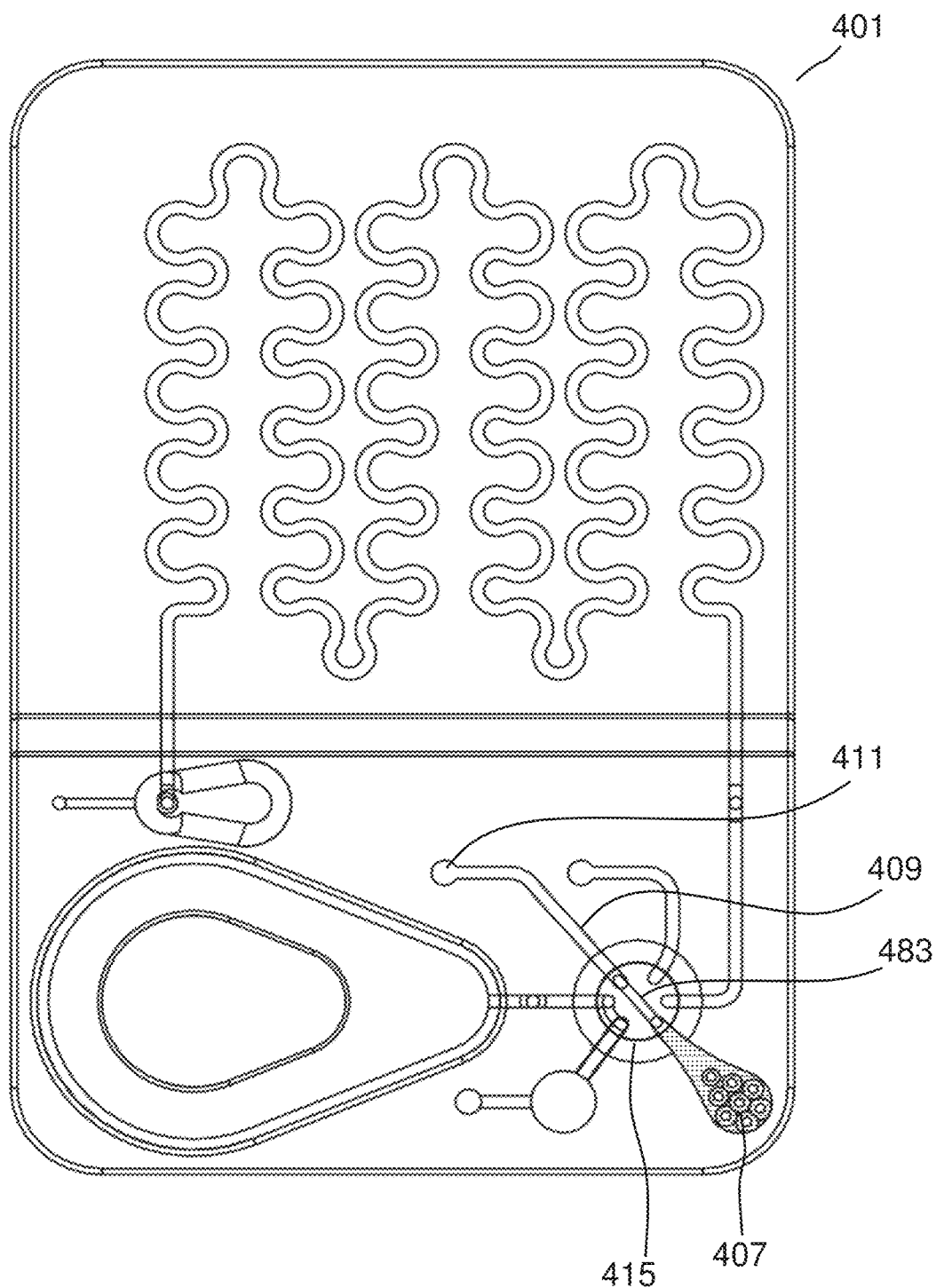
FIG. 8A is a plan view of an illustrative test cartridge showing a sample of whole blood deposited in the input port.
Figure 8B:
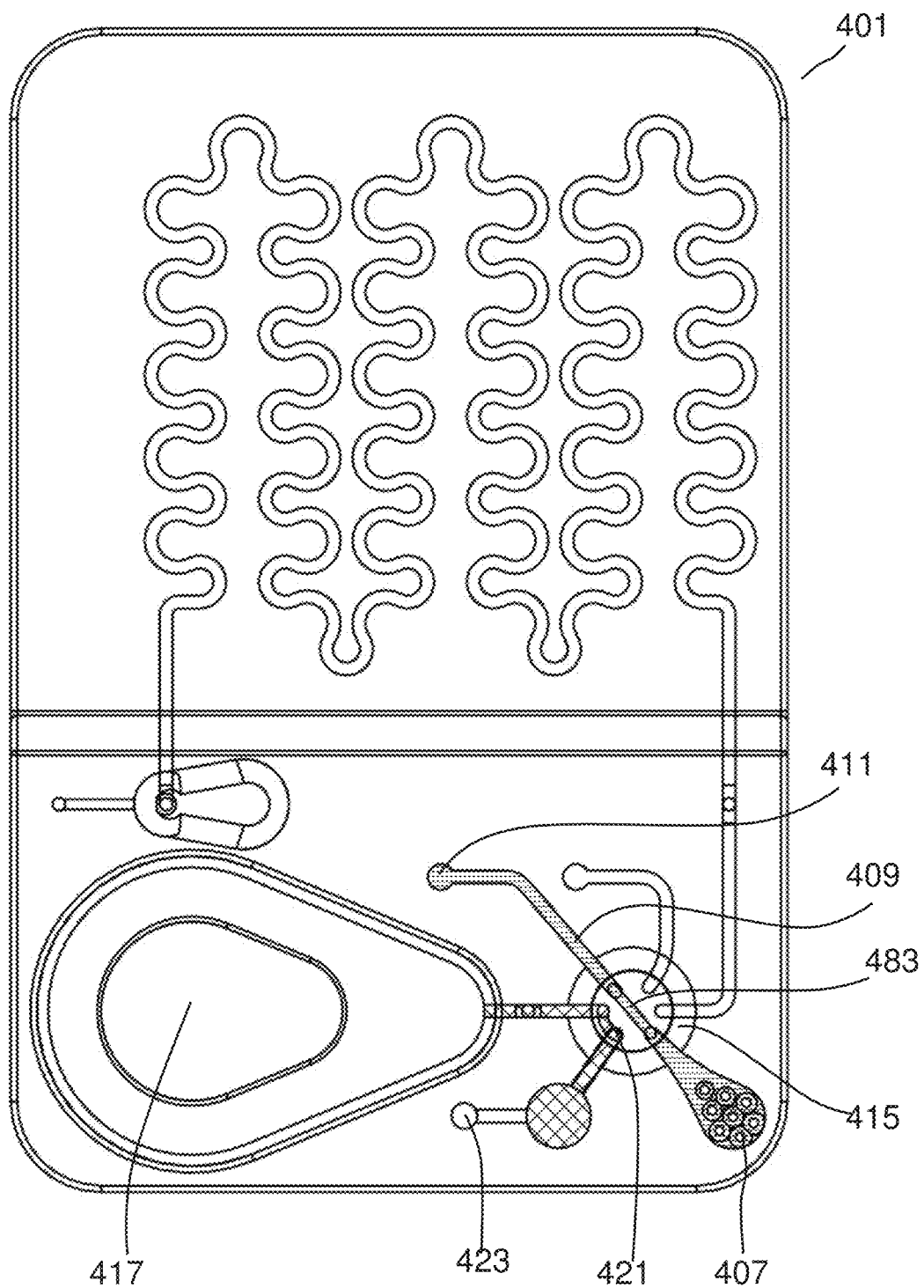
FIG. 8B is a plan view of the test cartridge of FIG. 8A showing initial movement of the sample and reagent with the rotary valve in the first open position.
Figure 8C:
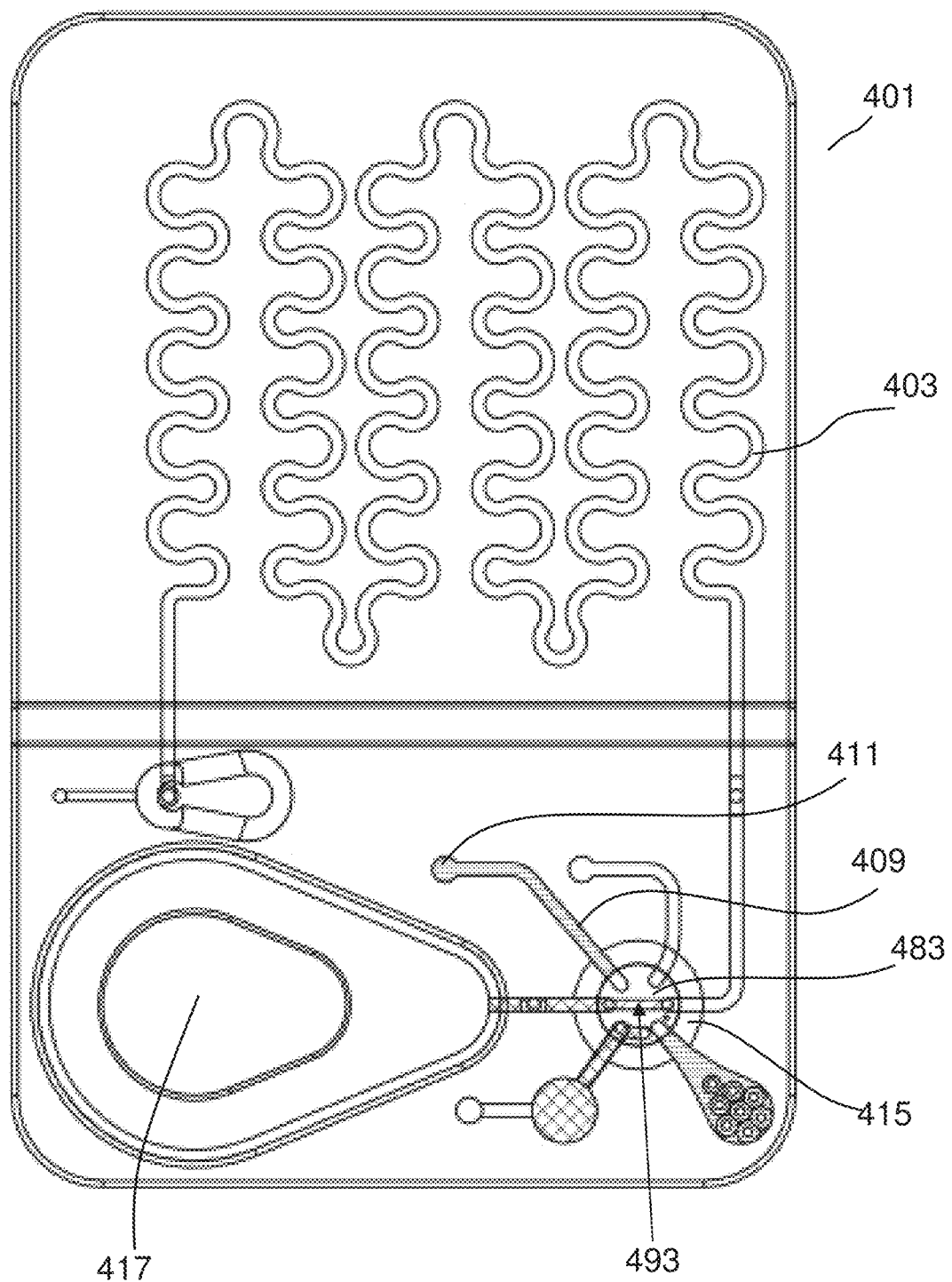
FIG. 8C is a plan view of the test cartridge of FIG. 8B with the valve in the second open position.

Turning our attention to FIG. 2 we will now describe the overall operation of cell analyzer 200 configured to provide a "CBC with Differential" analysis with reference to the test cartridge 401 illustrated in FIGS. 8A-8F and cell analyzer 200 illustrated in FIG. 1. Prior to adding the blood sample from a patient presented at box 500 to the test cartridge, the user first obtains a new test cartridge 401 at box 505 and opens it to expose the input port 407. Blood from a finger prick is applied to an input port 407 on the cartridge (see FIG. 8A) at box 510 and the input port 407 is covered. The user inserts the test cartridge into the cell analyzer 200 at box 515. The test cartridge is moved into the analyzer where mechanical and fluid connections are made between the analyzer and the cartridge as described above with reference to FIG. 1. As a first step of analysis, the sample is drawn into the metering chamber passing through and into a photometric chamber 409 (FIG. 8A). Absorbance of the blood is measured at box 520. Data from absorbance measurements are used to determine hemoglobin concentration. At box 530 sample in the metering chamber 483 is imaged using monitoring camera 255 and analyzed to confirm that the metering chamber was properly filled at box 535. If an error is detected the analysis is terminated at box 537 and the user is alerted to the error and instructed to remove the cartridge and reject the test.

Figure 8D:
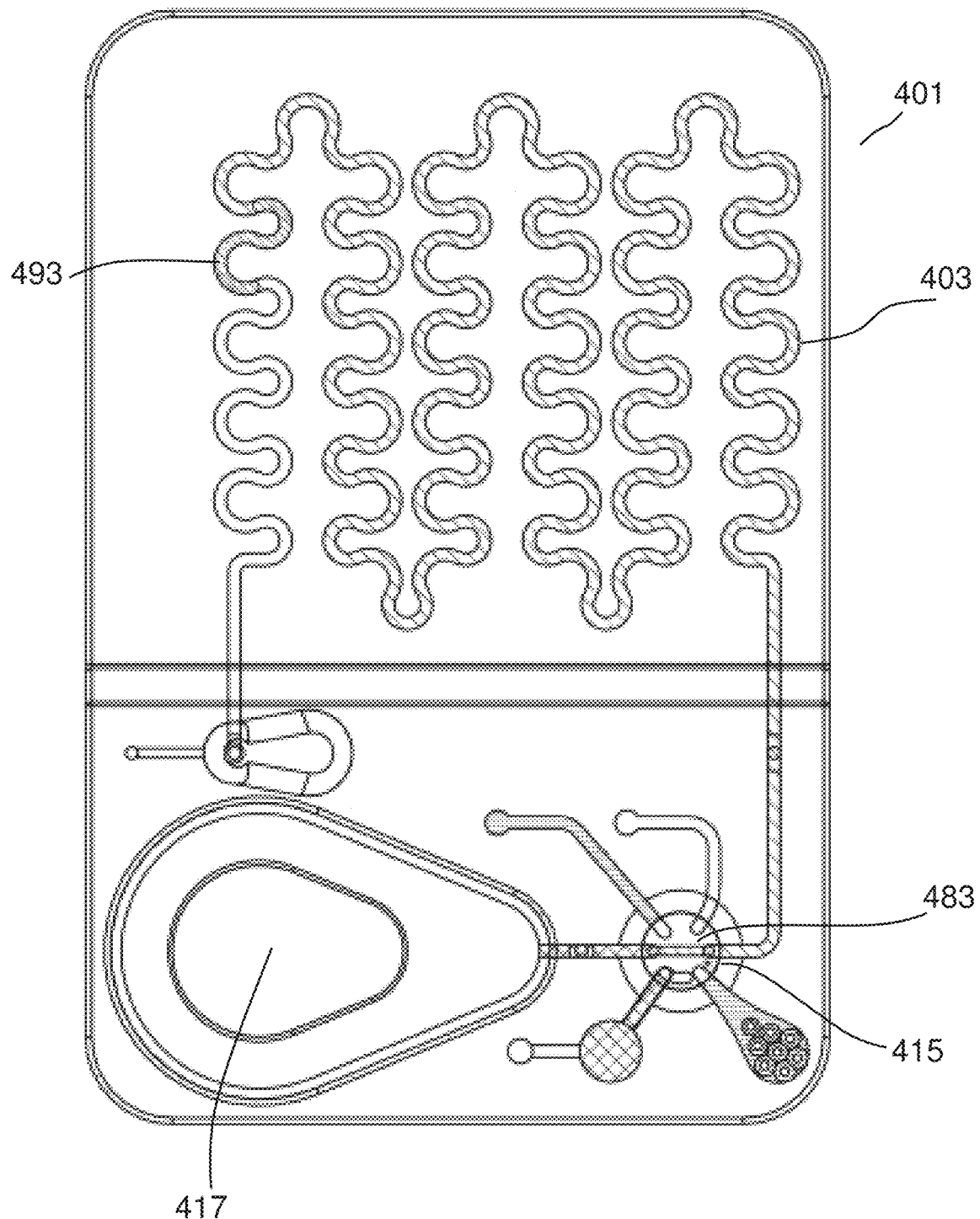
FIG. 8D is a plan view of the test cartridge of FIG. 8C illustrating the sample and the reagent in the imaging chamber.

If the pass-through conduit 413 is correctly filled the diluent/reagent channel is primed at box 540 as described above with reference to FIG. 8B. Rotary valve 415 is then turned to the position shown in FIG. 8C to isolate the sample and to allow diluent/reagent to wash the metered volume of blood out of the pass-through conduit 413 at box 545 while being imaged by monitoring camera 255. The transfer continues until the monitoring camera 255 confirms that diluent/reagent plus sample has almost filled the imaging chamber as illustrated in FIG. 8D.

Figure 8E:
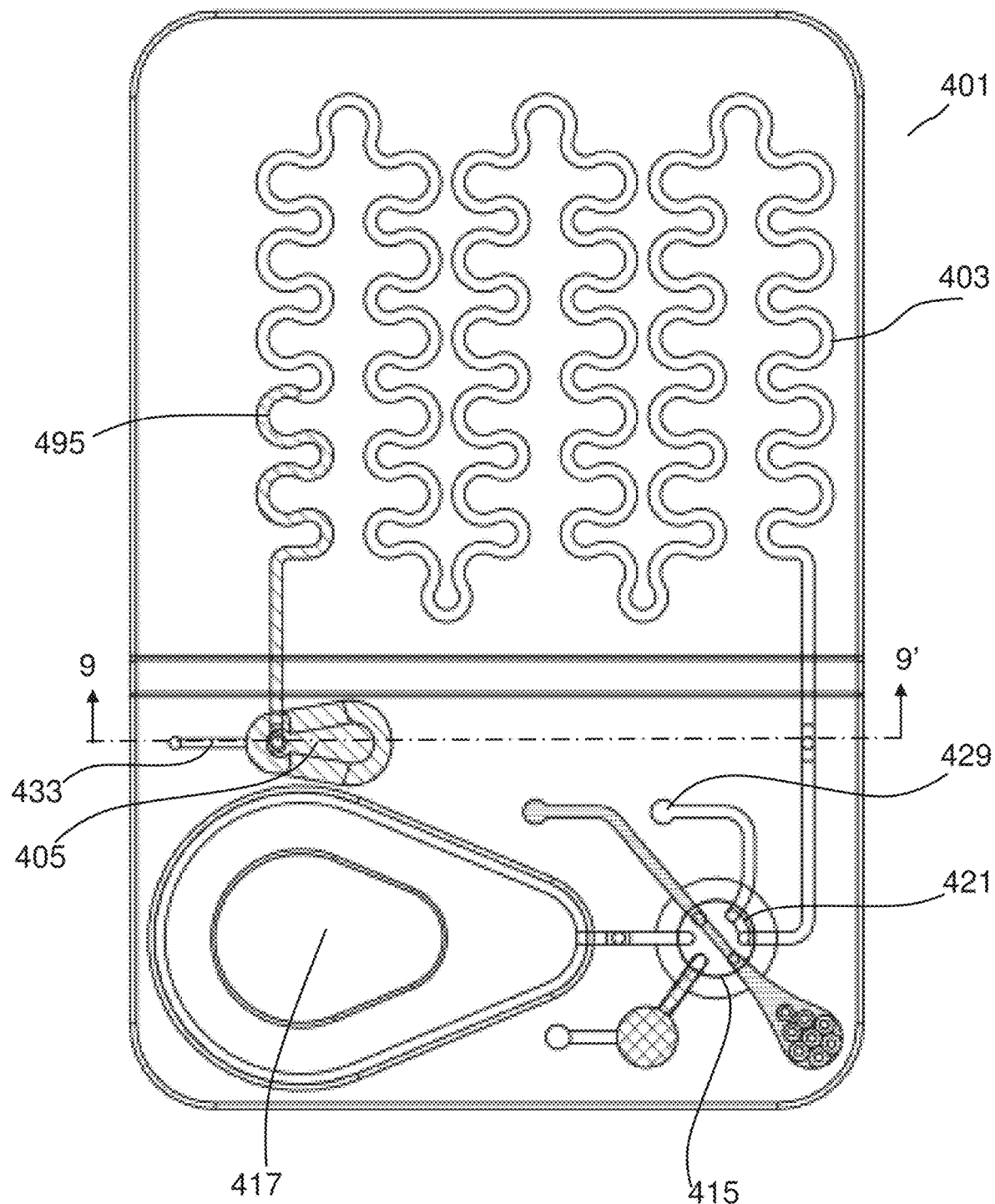
FIG. 8E is a plan view of the test cartridge of FIG. 8D illustrating the sample and most of the reagent positioned in the mixing chamber.
Figure 8F:
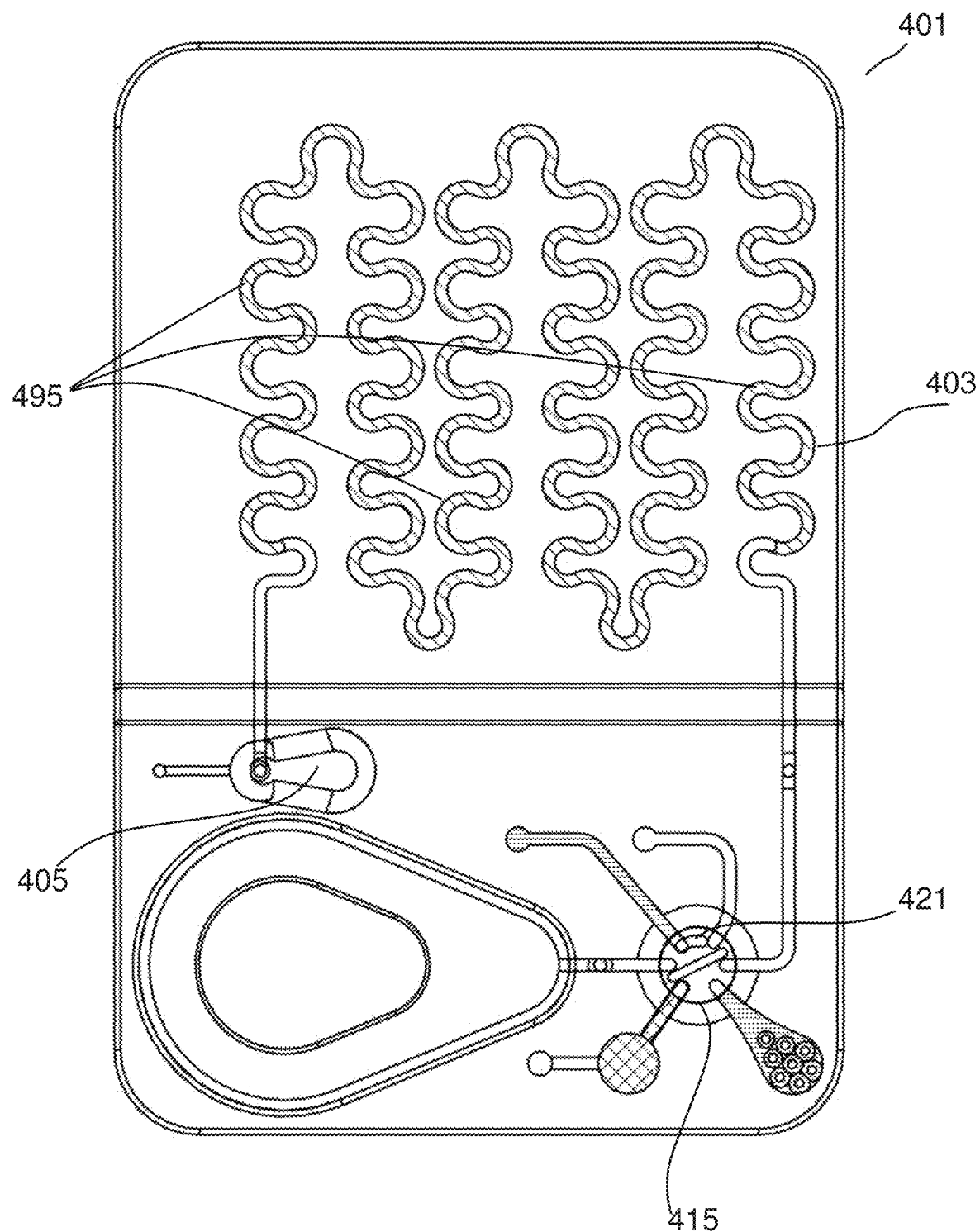
FIG. 8F is a plan view of the test cartridge of FIG. 8E illustrating all of the sample and the reagent positioned in the imaging chamber and the valve in a final position.

Once a sufficient volume of diluent/reagent is transferred, rotary valve 415 is positioned as shown in FIG. 8E and the total volume of sample and diluent/reagent is mixed, 550. At box 555 the entire volume 495 is transferred to the imaging chamber and rotary valve 415 is positioned as shown in FIG. 8F. Note that by transferring the entire volume of mixed sample 495, all of the metered volume of blood from the original sample plus the unmetered volume of diluent/reagent is positioned in the imaging chamber at box 555.

If test cartridge 400 is used, it is inserted into cell analyzer 200 and analysis begins at step 560. Analysis of test cartridge 401 or 402 continues at step 560 when the x-y stage 225 moves the test cartridge 401 to obtain bright-field and fluorescent images of the entire imaging chamber 403 at box 560. In an alternate embodiment, objective lens 265 and/or digital camera 280 are moved and test cartridge 401 remains stationary. In yet another embodiment objective lens 265 has sufficient field of view to capture the entire imaging chamber 403 without movement. Two digital images of each physical frame of the imaging chamber are transferred to image processor/computer 290 at box 565. One image, taken with bright-field optics, can be compared to the other image taken with fluorescent optics to identify red blood cells, white blood cells and platelets. Further analysis of the white cell sizes and internal structure can identify sub-types of white cells using pattern recognition.

At box 570 comparison of the bright-field and fluorescent images can differentiate mature red cells from reticulocytes and nucleated red blood cells. By dividing each cell count by the known volume of the metering chamber 483, the concentration (cells per unit volume) can be determined. By using a sphering agent the planar sizes of red cells can be transformed into mean corpuscular volume (MCV). Combining the red blood cell count with MCV and the volume of the metering chamber 483 allows the calculation of hematocrit (HCT) and red cell distribution width (RDW).

Further calculations using the separately measured HGB from box 525, combined with the RBC count gives mean corpuscular hemoglobin (MCH), and mean corpuscular hemoglobin content (MCHC).

At box 575 the measured results are compared with previously defined limits and ranges for the particular patient population and determination is made whether the results are within or outside normal expected ranges. According to this determination results within normal ranges are reported in box 580 and results that are outside the normal ranges are reported in box 585. As will be discussed in more detail below, the cell analyzer 200 can also perform a variety of other quality control and calibration operations to ensure the accuracy of its results using the microscope and/or the monitoring camera(s).

II. Control Material

Referring to FIG. 3, some of the quality control and calibration operations employ a surrogate control material. An illustrative surrogate control material 600 can consist of a dye 602 and beads (e.g., 604, 606, 608, 610, 612) of various sizes, shapes, and/or colors in the dye. The dye is chosen such that the concentration and absorbance simulates whole blood at at least one wavelength of light. The beads may be made of any suitable material, including silica, polystyrene, or other polymer in composition. The beads could also be coated with a metal such as gold or silver. The sizes of the beads are typically in the range of 1-20 micrometers to simulate the size of platelets, red blood cells, reticulocytes, and white blood cells. Some or all of the beads may be fluorescent to aid in detection. The beads may be varied in shape and/or color to allow for a white cell differential to be reported. A variety of different shapes can be used, including spheres, raisin, raspberry, pear, peanut, snowman, oblong, or rod shaped. Beads of different shapes and characteristics can be obtained, for example, from Bangs Laboratories, Inc., MAGSPHERE, and Microspheres-Nanospheres (a Corpuscular Company).

Figure 3A:
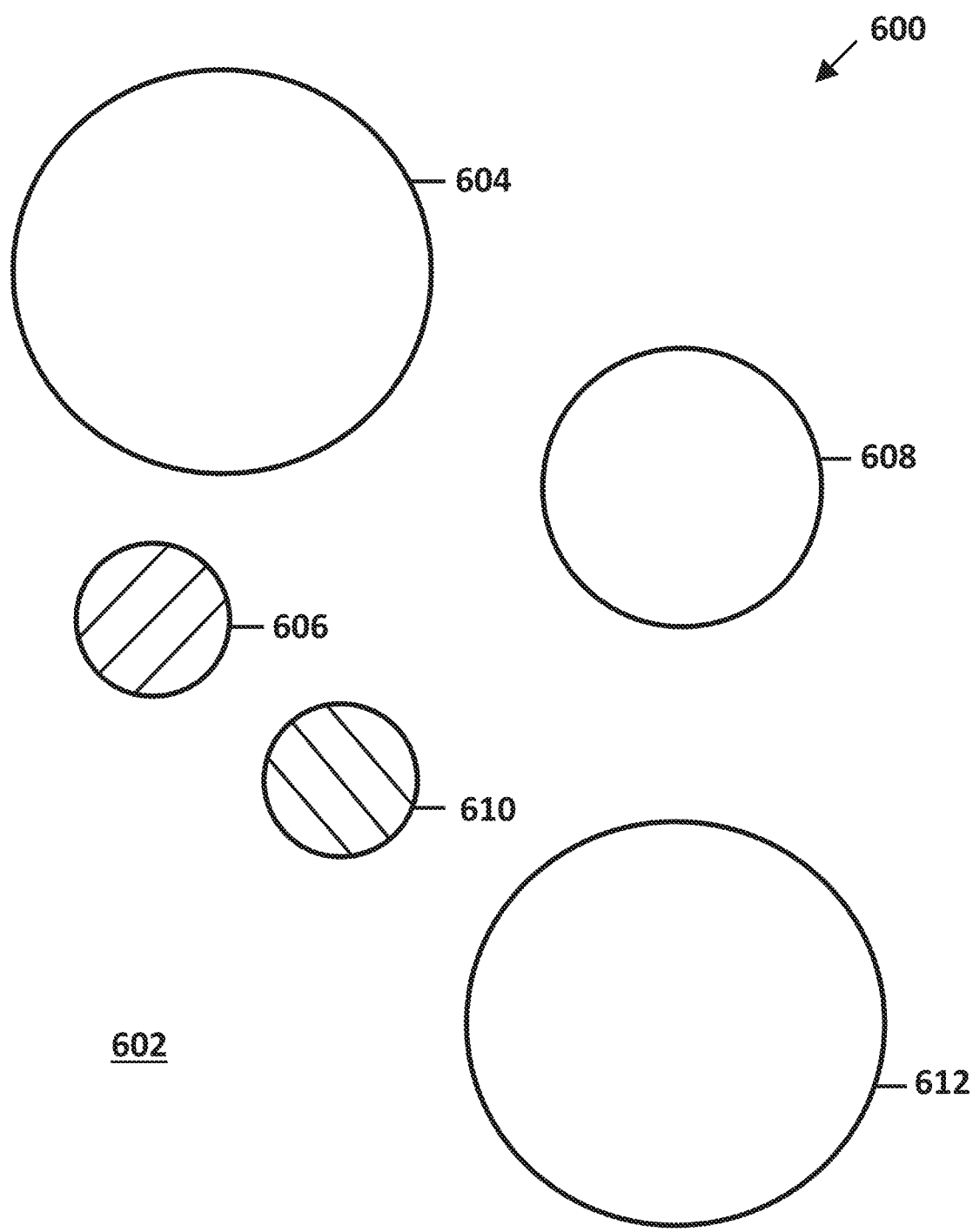
FIG. 3A is a schematic image of an illustrative quality control material that can be used with cell analyzers, such as the microscope-based analyzer of FIG. 1.
Figure 3B:
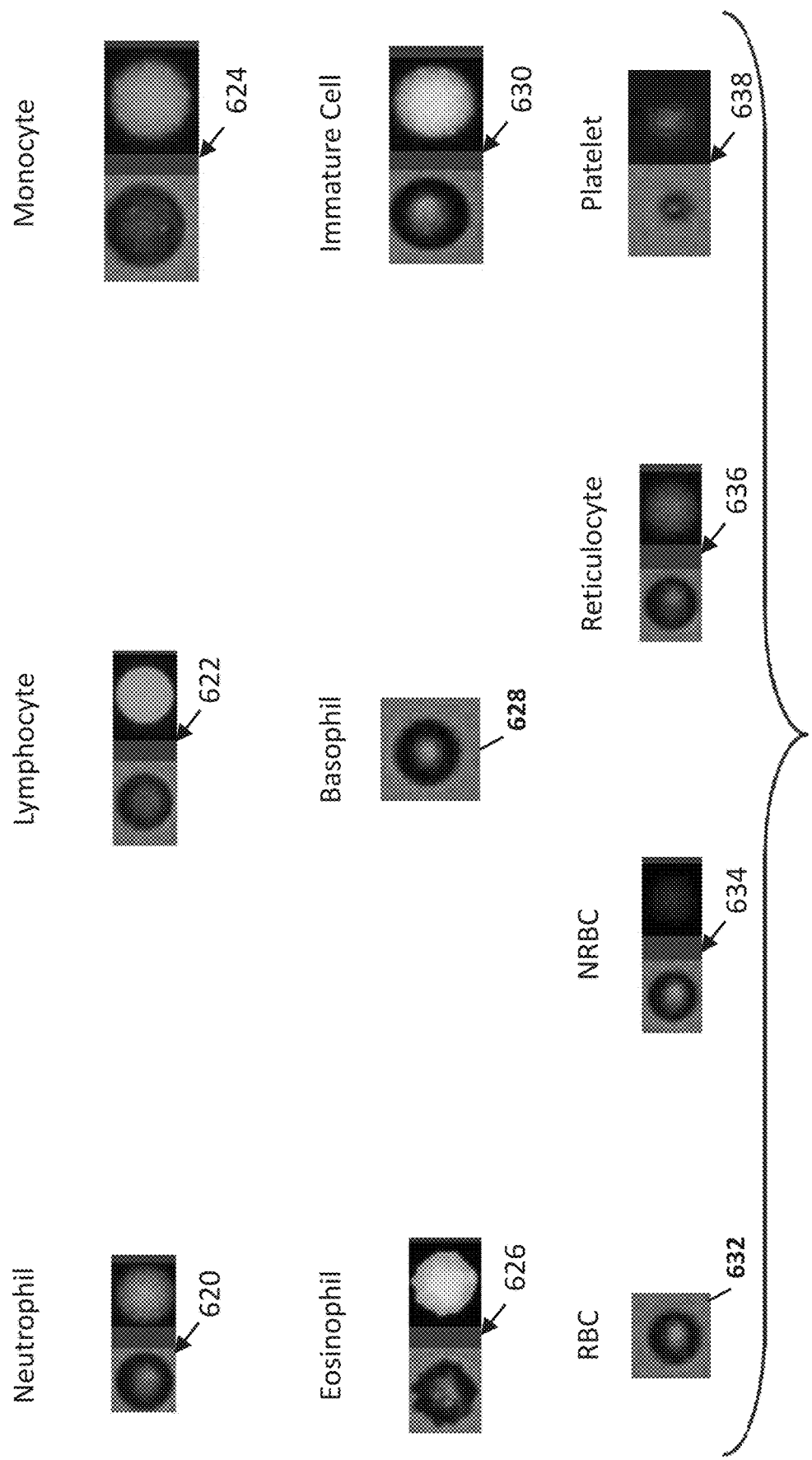
FIG. 3B is a set of bright-field and fluorescent microscopic images of microparticles used to simulate various cell types for use in a quality control material.

Referring to FIG. 3B, an illustrative set of beads for a surrogate control material that can be used to perform CBC tests includes a variety of beads in which size, shape, and color are used to simulate various characteristics of cells, as presented in Table 1. In the figure, images of the beads are shown in pairs with color microscopic images on the left and corresponding fluorescent microscopic images on the right. No fluorescent image is shown for the basophil and Red Blood Cell (RBC) beads because these beads don't fluoresce. Image processing can be used to determine the size, shape, bright-field (BF) color, and fluorescence (FL) color of the beads.

TABLE 1

| Ref. | Name | Analog | Size | Shape | BF color | FL color |
|------|------|--------|------|-------|----------|----------|
| 632 | Red Blood Cells | RBC | 5 μm | round | none | none |
| 634 | Nucleated Red Blood Cells | NRBC | 5 μm | round | none | green |
| 636 | Reticulocyte | RET | 5 μm | round | none | red |
| 620 | Neutrophil | NEU | 7 μm | round | none | orange |
| 622 | Lymphocyte | LYM | 7 μm | round | none | green |
| 624 | Monocyte | MON | 10 μm | round | none | green |
| 626 | Eosinophil | EOS | 7.25 μm | raisin | none | green |
| 628 | Basophil | BAS | 7 μm | round | red | none |
| 630 | Immature Cell | IC | 10 μm | round | none | orange |
| 638 | Platelet | PLT | 3 μm | round | none | green |

The beads in the surrogate control material presented above can be selected in such a way as to simulate a normal whole blood sample. But they can also be selected in ways that simulate conditions that simulate an abnormal whole blood sample. In one embodiment, the control material is supplied in several lots with different count levels, including one normal count, one low abnormal count, and one high abnormal count.

III. Calibration

Because the surrogate control material can be designed with a known concentration of beads, a count of these beads acts as a standard that can be used to derive one or more calibration values for the instrument and/or cartridge. These values can be used to adjust one or more aspects of measurements to be made on actual blood samples. One example of a count-based calibration value is a calibration factor that can adjust for the actual metered volume of a sample. If actual metered volumes are 5% smaller than expected, for example, count results can be multiplied by a corresponding factor to adjust for the discrepancy. Other aspects of the measurement can also be adjusted for using factors, offsets, and/or other adjustment formulas. The dye 602 can be used in calibration operations, as well, such as to allow the analyzer to derive calibration values for photometric measurements. Bead color and shape can also be used as known properties in deriving calibration values for the optics or the camera.

Figure 4:
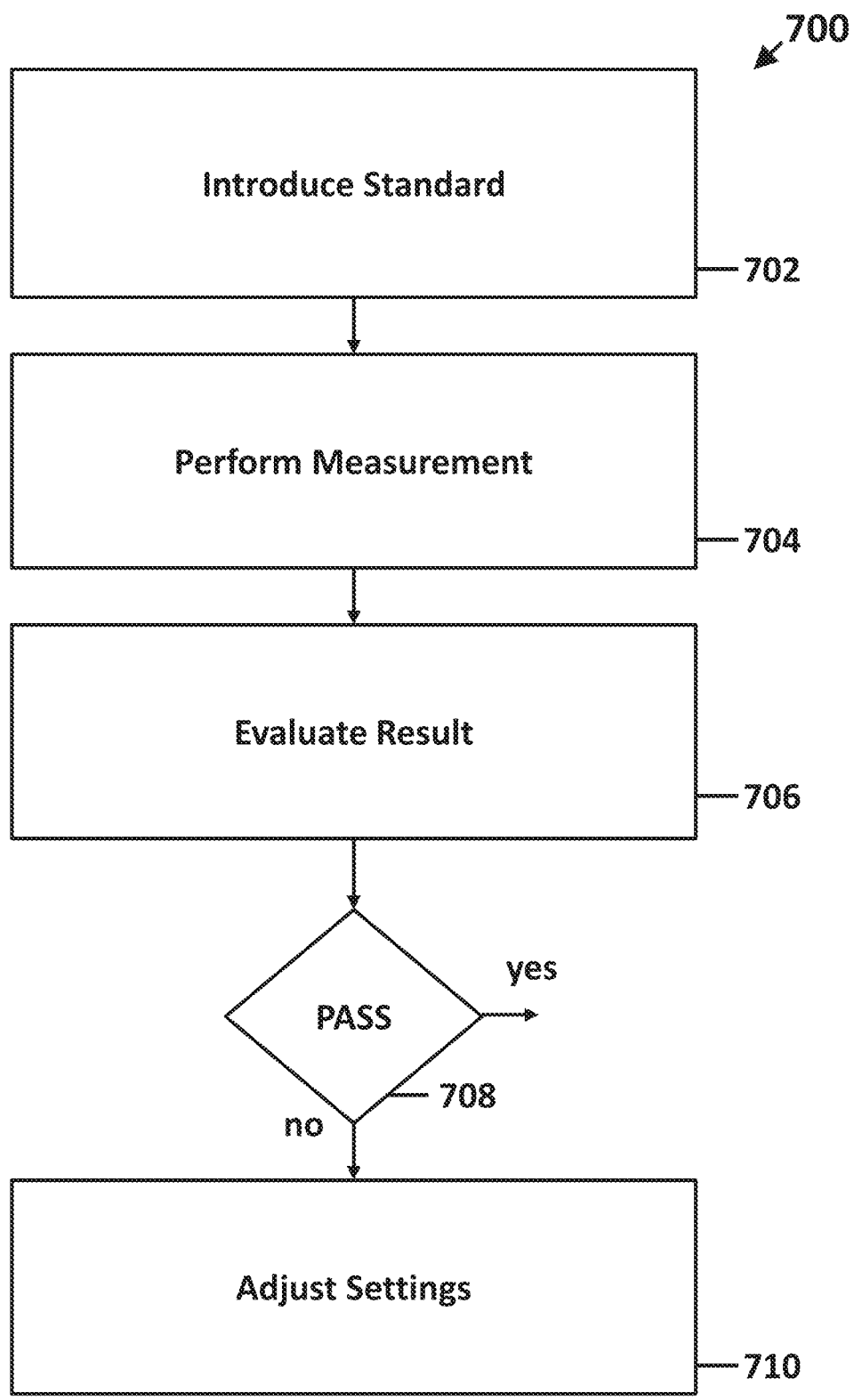
FIG. 4 is a flowchart of an illustrative calibration method for the a cell analyzer, such as the microscope-based analyzer of FIG. 1.

Referring to FIG. 4, the cell analyzer 200 can be calibrated when it is first set up, and it can then be recalibrated periodically thereafter. An initial calibration run 700 can involve introducing a sample of the surrogate control material 600 in the test cartridge 100 (step 702), and taking measurements (step 704). The result can then be used to adjust the operation of the analyzer or evaluated to determine whether any adjustments to the analyzer are needed (steps 706-710).

IV. Ongoing Quality Control Operations

The cell analyzer 200 can perform ongoing operations to improve a variety of aspects of its operation, including the accuracy, precision, and reliability of its measurements. As noted above, these operations can include performing calibration operations on a regular basis. They can also include ongoing monitoring of a variety of aspects of the analyzer's operation.

Figure 5:
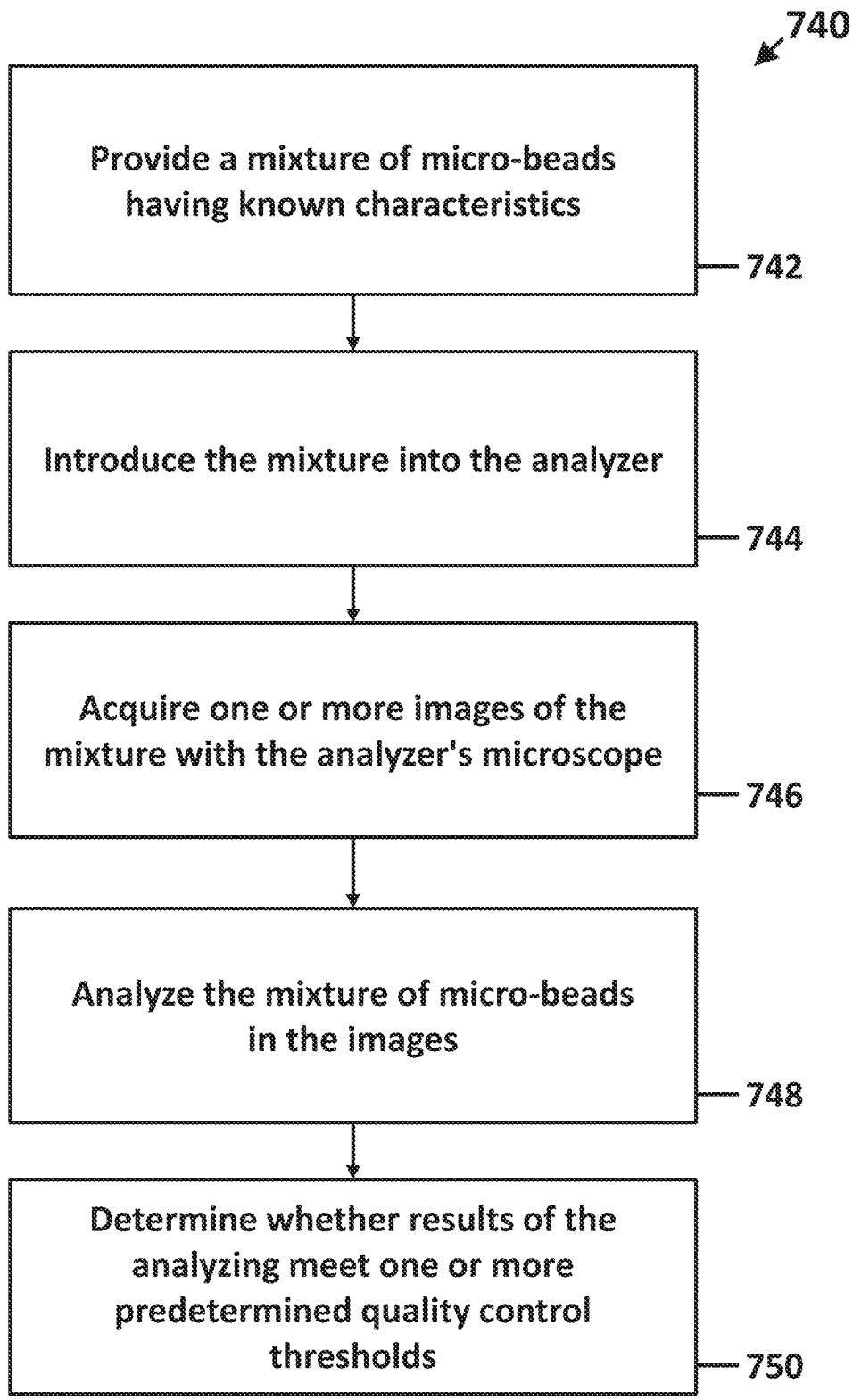
FIG. 5 is a flowchart of an illustrative method of verifying the operation of a cell analyzer, such as the microscope-based analyzer of FIG. 1.

Referring to FIG. 5, one type of quality control operation 740 is to use the surrogate control material 600 to determine whether one or more aspects of the cell analyzer 200 operates acceptably. This type of operation begins with providing a surrogate control material and introducing it into the analyzer (steps 742, 744). Images of the mixture are then acquired with the analyzer's microscope (step 746), and the analyzer analyzes these images (step 748). A determination is then made as to whether results of the analysis meet one or more predetermined quality control thresholds (step 750). If the thresholds are met, patient samples can be processed. If they aren't met, remedial measures must be taken on the analyzer, such as performing adjustments to the analyzer based on results of the determination, or by performing further calibration operations, or by performing technical service of the analyzer.

Figure 6:
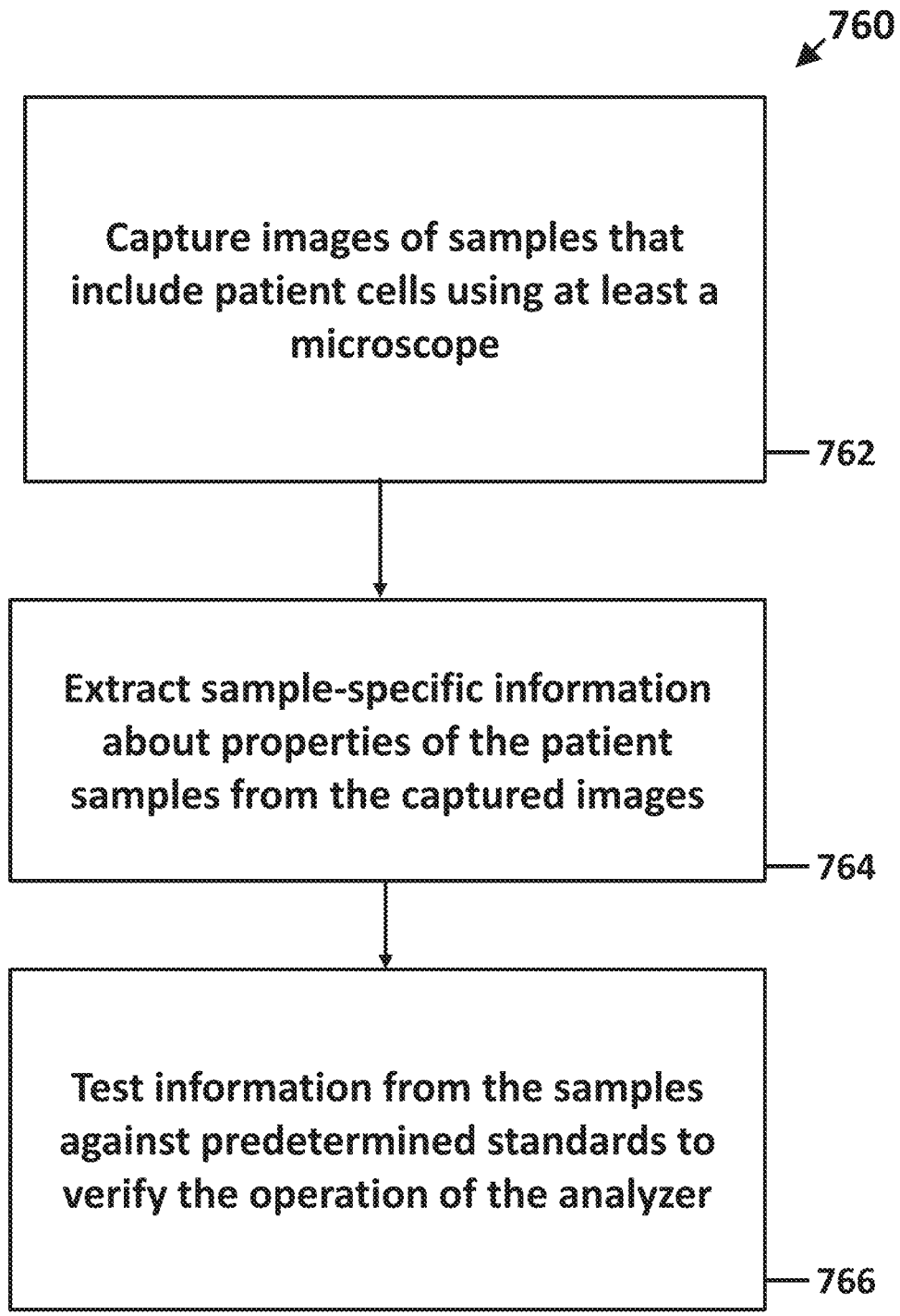
FIG. 6 is a flowchart of an illustrative quality control method that can be used with cell analyzers, such as the microscope-based analyzer of FIG. 1.

Referring to FIG. 6, another type of quality control operation 760 is to monitor the ongoing operation of the cell analyzer 200 as it processes patient samples. One way to do this is to capture and analyze images of the samples using the microscope and/or one or more monitoring cameras (step 762). Sample-specific information about properties of the patient samples can be extracted from the captured images (step 764), and tested against predetermined standards to verify the operation of the analyzer (step 766).

Figure 7:
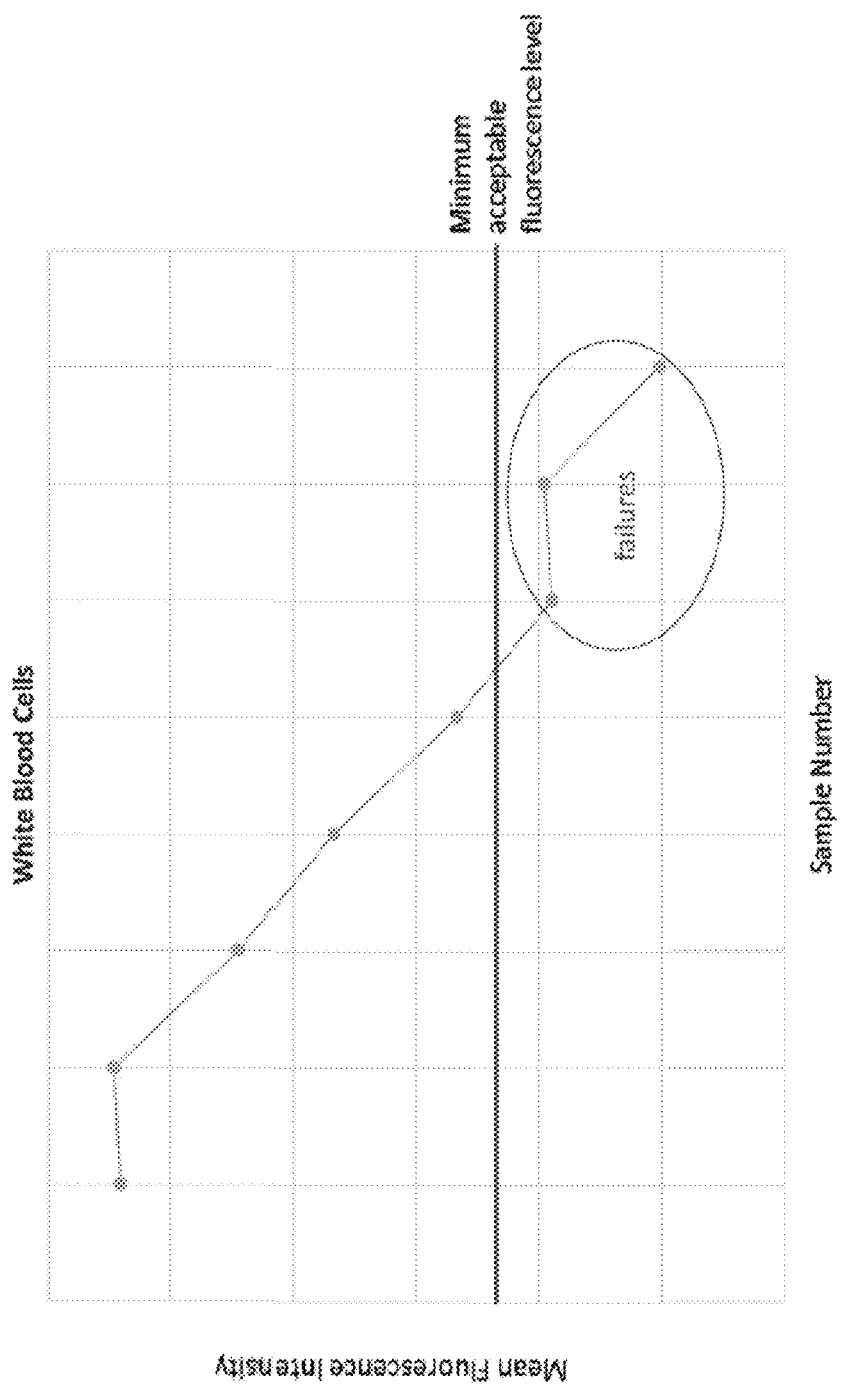
FIG. 7 is an illustrative plot of mean fluorescence intensity against time for eight illustrative sample runs with an acceptable excursion level for the mean White Blood Cell (WBC) fluorescence signal during a measurement performed by a cell analyzer, such as the microscope-based analyzer of FIG. 1.

Mean fluorescent intensity of cells can be monitored, for example, by comparing the detected fluorescence level to a pre-determined acceptable level to detect potential defects in fluorescence measurements, such as damage to the stain reagent or non-uniform staining. FIG. 7 shows the mean fluorescence for each of eight illustrative sample runs with an acceptable excursion level for the mean White Blood Cell (WBC) fluorescence signal during a measurement performed by the cell analyzer 200. When the mean fluorescence of the WBC falls below a pre-determined minimum, the test, or a certain parameter of the test, is rejected. In this example, all of the WBCs in the test were used to determine mean fluorescence. However, a subset of WBCs or a specific cell class, such as neutrophils, could be used to reject the test.

Figure 3E:
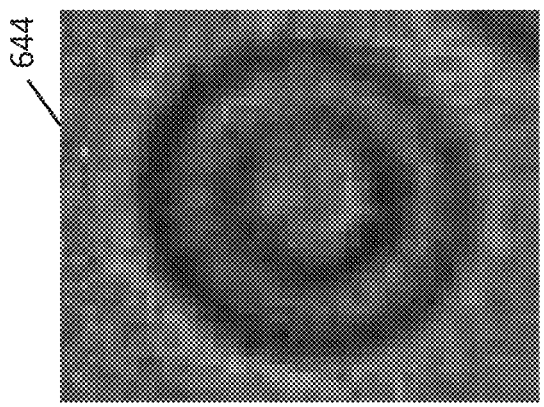
FIG. 3E is a microscopic image of a completely unsphered red blood cell that fails specification because of a secondary ring detected in the image.
Figure 3D:
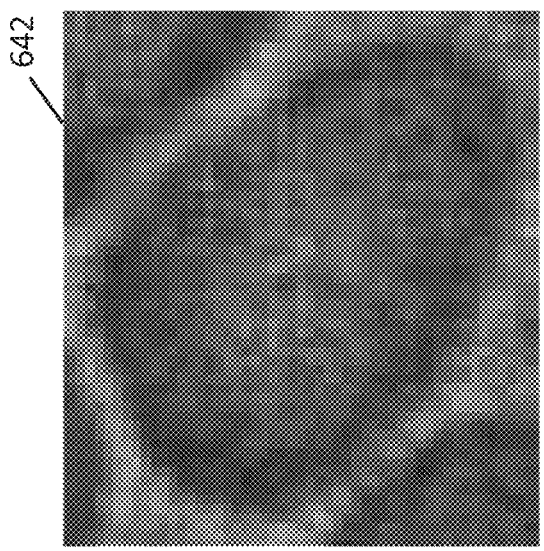
FIG. 3D is a microscopic image of an incorrectly sphered red blood cell that fails a roundness specification.
Figure 3C:
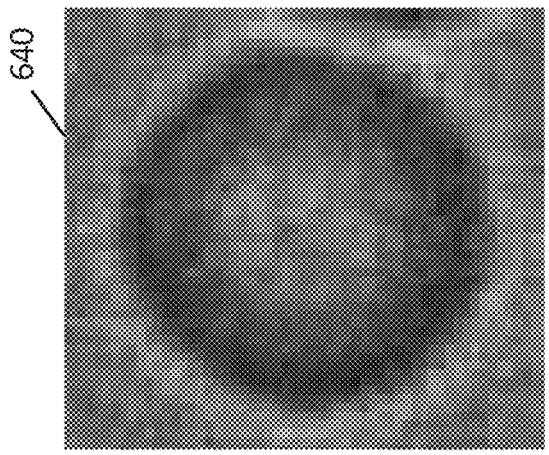
FIG. 3C is a microscopic image of a correctly sphered red blood cell.

Referring to FIGS. 3C-E, roundness of red blood cells can be compared to a pre-determined set of sphering criteria to verify that the red blood cells have been sphered correctly or detect if the sphering reagent was damaged or ineffective. This operation uses image processing to accept or reject a sample based on pre-determined sphering criteria, including roundness and secondary ring specifications. The image processing software will determine a properly sphered cell 640 and pass if it meets these specifications. An incorrectly sphered RBC 642 will fail the roundness specification. Roundness can be quantified by comparing the perimeter of the object and its area to known mathematical formulae for various geometric shapes. An unsphered RBC 644 will fail the secondary ring specification. The detection of a secondary ring as shown in FIG. 3E is due to the biconcave disc geometry of the unsphered RBC 644. The sample can also be checked for clots, voids, and microbubbles, by use of image processing software and comparing the features of these non-cellular artifacts to pre-determined characteristics. The software can also use image processing software to determine if the cells are crowded or overlapping, which condition could cause an error in counting. Further examples of tests are presented below.

V. Discussion

Traditional CBC analyzers typically must be calibrated for white blood cell count (WBC), red blood cell count (RBC), hemoglobin (Hgb), platelet count (Plt), mean cell volume (MCV), and mean platelet volume (MPV). All of these parameters are derived from the impedance part of the analyzer. There is generally no calibration for the flow cytometer, since it is typically only used to determine relative percentages, but not absolute counts. However, if absolute counts are determined by the flow cytometer rather than using an impedance counter, then the flow cytometer should be calibrated. Traditional CBC analyzers are typically calibrated every six months, or when there has been a critical part replacement, or if the quality control checks identify that the system is inaccurate. The calibrators are similar in composition to stabilized blood controls, although they typically have an even shorter shelf life and open-container use life. Traditional CBC analyzers are checked for calibration, because protein or salt buildup and cellular debris can cause shifts in size measurements (MCV, MPV) and in absorbance for the hemoglobin photometer (Hgb), and because changes to flow rates or dilution ratios can cause changes to the absolute count results (WBC, RBC, and Plt).

As discussed above, the use of stabilized blood is a compromise to provide a method of performing quality control. For years, this has worked quite well for impedance and flow cytometry technologies, but it is not optimal for other technologies, such as microscopy.

Microscopy-based cell imaging and counting systems are subject to different calibration needs than traditional CBC systems. Where an imaging system comprises an analyzer and a single-use test cartridge, the system can be factory calibrated and not require regular calibration. The use of a single-use test cartridge eliminates the possibility of carry-over, blockages, or protein buildup. The absolute count parameters—WBC, RBC, and Plt—are determined by the sample volume in the single-use disposable test cartridge metering valve. The cell sizing parameters—MCV and MPV—are measured and determined by the lenses and the pixel size of the camera, neither of which will generally change over time. The hemoglobin photometer is calibrated at the factory and is not usually at risk of drift because it maintains a dry interface with the disposable test cartridge. The photometer can be calibrated using a dye or film with a known absorbance value at the measurement wavelength(s) used for the hemoglobin measurement. The depth of the hemoglobin chamber in the cartridge is also a determining factor in the Hgb result, which is controlled in the manufacturing process. The same holds true with the with the test cartridge metering valve volume.

Traditional CBC analyzers use control material for all of the measured parameters. Table 2 lists common error modes of traditional CBC analyzers and how a stabilized blood control is used to help mitigate the error. This is not an exhaustive list, but it does show the need for a control material with absolute counts, sizing parameters, and WBC differential in order to verify that traditional CBC systems are in good working condition.

TABLE 2

Common errors in traditional hematology analyzers and control methods to identify them.

| Error Mode | Cause(s) | QC Verification |
| --- | --- | --- |
| blood cells settle | operator fails to mix sample tube | accuracy of RBC, WBC, plt |
| blood sampling and metering | fluidics, metering mechanism | accuracy of RBC, WBC, plt |
| dilution ratio | fluidics | accuracy of RBC, WBC, plt |
| RBC sphering | reagent integrity, fluidics | accuracy of RBC, MCV |
| RBC lysing | reagent integrity, fluidics | accuracy of WBC, Hgb |
| Hgb reagent (species conversion) | reagent integrity, fluidics | accuracy of Hgb |
| Hgb calibration | fluidics, cleanliness of Hgb chamber | accuracy of Hgb |
| cell size calibration | fluidics, cleanliness of counting chambers | accuracy of MCV, MPV |
| cell count calibration | fluidics, cleanliness of counting chambers | accuracy of RBC, WBC, plt |
| WBC differential (impedance) | fluidics, cleanliness of counting chambers, partial block | accuracy of 3-part WBC Diff (GRN %, LYM %, MON %) |
| WBC differential (flow cytometry) | fluidics, cleanliness of flow cytometer, partial block | accuracy of 5-part WBC Diff (NEU %, LYM %, MON %, EOS %, BAS %) |

Proposed is a combination of a surrogate blood control and a system of internal software checks that can be utilized to ensure accurate performance of microscopy-based cell imaging and counting systems. The quality control material is supplied in three levels, similar to those that would be used with blood-based controls. The material consists of a dye and beads of various sizes, shapes, and/or colors. The dye or plurality of dyes is chosen such that the concentration and absorbance simulates whole blood at least at one wavelength of light. The beads may be silica, polystyrene, or other polymer in composition. The sizes of the beads are typically in the range of 1-20 micrometers to simulate the size of platelets, red blood cells, reticulocytes, and the different white blood cells. Some or all of the beads may fluoresce to simulate WBCs, platelets, or reticulocytes. The beads may be varied in shape and/or color to simulate a white cell differential to be reported.

When used in conjunction with a single-use test cartridge, a drop of quality control material is deposited by the user into a test cartridge in the same way that a patient sample is deposited. No special quality control test cartridge is required. The quality control material is analyzed in the cartridge with the same process as a patient sample.

When the image-based system does not use a single-use cartridge, or if the test cartridge does not contain all of the fluidics needed for the test, the analyzer can aspirate the QC sample, in the same way that it aspirates a whole blood sample. The use of a surrogate control material can be particularly useful in systems, where the fluidics are part of an analyzer.

Table 3 is a list of the error modes that could arise in performing a CBC test. Two methodologies are presented: one using a whole blood control (if one existed that could meet the need for microscopy) and the other using the new control comprising of a daily surrogate control material and internal software quality controls. The use of software controls on every sample is particularly important for single-use test devices.

TABLE 3

Failure modes on a Microscopy-Based Cell Imaging and Counting System with a single-use test cartridge and how surrogate controls and software controls are used to identify errors.

| Error Mode | Cause(s) | Whole Blood Control Methodology | New Control Methodology |
| --- | --- | --- | --- |
| blood cells settle | operator fails to mix sample tube | if not mixed, cells settle in tube | if not mixed, beads settle in tube |
| blood cells settle | operator fails to start test within 1 minute | cells settle in sample input | beads settle in sample input |
| blood sample metering | consumable failure | accuracy of measured absolute counts of cells | accuracy of measured absolute counts of beads |
| metering diluent/stain | pneumatics failure | accuracy of measured absolute counts of cells | accuracy of measured absolute counts of beads |
| mixing blood and diluent | consumable failure | cell distribution | bead distribution |
| transfer of mixed sample to imaging region | pneumatics failure | cell distribution | bead distribution |
| homogeneity of sample in imaging region | pneumatics failure | cell distribution | bead distribution |
| WBC count | reagent integrity, consumable failure | cells fluoresce and can be counted | beads fluoresce and can be counted |
| WBC differential | reagent integrity, consumable failure | WBC sub-populations stain differently, creating a differential | monitor mean fluorescence on every sample |
| RBC count | reagent integrity, consumable failure | cells are counted in bright-field | beads are counted in bright-field |
| MCV measurement | reagent integrity | RBC are sphered and measured | monitor cell sphering on every sample, measure size of beads |
| platelet counting | reagent integrity, consumable failure | platelets fluoresce and can be counted | beads fluoresce and can be counted |
| hemoglobin measurement | reagent integrity, consumable failure | reagent-free, measured on hemoglobin of control | reagent-free, measured on dye of control |

Traditional CBC analyzers generally use stabilized whole blood control materials to perform a QC check on the white cell differential. For a three-part differential using impedancemetry, any drift or partial clog in the impedance channel could cause erroneous results in the three part differential. Similarly for flow cytometers, a partial occlusion in the injector nozzle to the flow cell can cause the stream of cells to be off center, thus causing erroneous results in the five-part differential. to be In a system that does not have fluidics or possible mechanical failures, the primary cause for a failed WBC differential would be a failure of the stain reagent. Monitoring the mean fluorescence on every sample can identify a problem with reagent or stain integrity on every cartridge. This is preferable to using quality control material to perform a QC check once per day.

The control material can also be used to check operator proficiency. Before a blood sample is run on a CBC analyzer, it should be properly mixed by the operator. If the operator fails to mix the blood sample, the analyzer could generate an erroneous result. QC material can be used to verify operator proficiency in mixing of the blood sample, as the beads will settle in the same manner that blood cells settle, and generate an erroneous result.

A set of internal process and system controls that are performed on every sample using quality control cameras can be used to further control cell imaging and counting systems. The cameras ensure that every part of sample preparation is performed correctly for every test. Table 4 details the procedural controls.

All operational steps—including sample metering, dilution, analysis, and analyzer self-checks are handled and controlled automatically within the device, without the need for user intervention. The analyzer performs self-checks during initialization to ensure that the system is working properly. These self-checks include the processors, the cameras, the safety interlocks, the microscope stage, and the diluter mechanism.

The single-use test cartridges are managed through barcode intelligence. Embedded within the barcodes are the lot number, the expiration date, and the serialization for each cartridge. When the cartridge is inserted, the analyzer reads the barcode automatically, eliminating the possibility of using an invalid cartridge, using an expired cartridge, or using a test cartridge more than once. Intelligence can also be managed by use of RFID tags, 1-Wire, iButton, EEPROM, or similar devices.

The system uses one or more quality control cameras for comprehensive monitoring of all sample processing steps. In the example of using two cameras, one quality control camera is used to verify that the metered blood sample is free from bubbles and that the metering process is accurate, without any loss of sample. This ensures that the metered volume of blood in every sample is accurate. This same quality control camera ensures that the entire sample from the mixing chamber has been emptied into the imaging chamber at the completion of the dilution step. The second quality control camera views the entire imaging chamber of the cartridge. This allows for the verification of the dilution integrity. If there are any bubbles or voids in the channel, the software automatically masks these sections and removes them from the calculation. The combination of these two cameras ensures that the metering and dilution on every cartridge is completely controlled and verified.

A third camera is part of the microscope and is used for analyzing the images of the cells at 20× magnification. In addition to the cell counting, sizing, and classification, this camera also verifies sample integrity at a microscopic level. For example, the software checks the images for clots and microbubbles and for overlapping cells. If the camera detects a problem with sample integrity, the analyzer will reject the sample. A different magnification could be used to analyze the quality of the cells and the fluid matrix.

TABLE 4

Procedural failure modes on the Microscopy-based Cell Imaging and Counting System and internal software checks are implemented as verification or cause for rejection.

| Error Mode | Software Process Control |
| --- | --- |
| insufficient blood sample | QC camera verification, reject |
| air bubbles in blood sample | QC camera verification, reject |
| test slide loading | mechanical design for fail-safe insertion of the test slide |
| metering blood sample | QC camera verification |
| metering diluent/stain | controlled by edge detectors, QC camera verification |

TABLE 4-continued

Procedural failure modes on the Microscopy-based Cell Imaging and Counting System and internal software checks are implemented as verification or cause for rejection.

| Error Mode | Software Process Control |
| --- | --- |
| washout of valve | QC camera verification |
| mixing blood and diluent | cell distribution, QC camera verification |
| transfer of mixed sample to imaging region | cell distribution, QC camera verification |
| homogeneity of sample in imaging region | cell distribution, QC camera verification |
| determine percent sampling of the whole | use QC camera to verify area |
| voids or bubbles in the imaging chamber | use QC camera to adjust area |
| clots or microbubble in the imaging chamber | use microscope camera to detect |
| overlapping cells | use microscope camera to detect |
| cartridge reuse or misuse | unique barcoded serial # for each cartridge |
| reagent quality | stability tracking by barcode |

Some or all of the various quality control and calibration tasks performed by the analyzer can be carried out using a specially programmed general purpose computer, dedicated hardware, or a combination of both. These can be incorporated into the analyzer as part of the system controller 250 and/or image processor/computer 290. Some or all of the control, image processing, calibration, and other functionality can also be provided through software and/or hardware logic provided by a standalone processing system located proximate the system. And parts of the functionality can even be provided from a remote location through a public or private communication network. In one embodiment, the system is based on stored software instructions running on a Microsoft Windows®-based computer system, but other platforms could be used as well, such as Android®-, Apple®-, Linux®-, or UNIX®-based platforms.

The present invention has now been described in connection with a number of specific embodiments thereof. However, numerous modifications which are contemplated as falling within the scope of the present invention should now be apparent to those skilled in the art. For example, while many of the techniques and materials described in this application are particularly well suited to use with microscopy-based analyzers, many of them may also be applied to quality control and calibration of traditional types of CBC analyzers. Therefore, it is intended that the scope of the present invention be limited only by the scope of the claims appended hereto. In addition, the order of presentation of the claims should not be construed to limit the scope of any particular term in the claims.

What is claimed is:

1. A method of verifying the operation of a cell analyzer having an automated microscope and image processing software for counting and analyzing cells and platelets in blood and which utilizes a test cartridge having a diluent/and or stain, the method comprising:
 a) introducing into the test cartridge a mixture of 1) a plurality of a first type of micro-beads in a known amount of solution having a first known characteristic and a concentration that simulates a concentration of a first type of cells in blood and 2) a plurality of a second type of micro-beads in a known amount of solution having a second known characteristic and concentration that simulates a concentration of a second type of cells in blood;

b) interfacing the test cartridge with the cell analyzer;
c) separating a known amount of the mixture of micro-beads from the remaining amount of the mixture of micro-beads in the test cartridge;
d) mixing the known amount of the mixture of micro-beads in the test cartridge with an amount of diluent and/or stain that is sufficient to form a substantially uniform mixture of micro-beads and diluent and/or stain, wherein the micro-beads are suspended therein;
e) transferring the entire mixture into the imaging chamber that is defined in the body of the test cartridge;
f) allowing the particles in the mixture to settle to a bottom of the imaging chamber;
g) capturing one or more digital images of the settled particles in the imaging chamber that are selected to be statistically representative of the number and distribution of the first and second types of micro-beads;
h) counting all of at least one type of micro-beads in the images using imaging processing software;
i) obtaining a number of micro beads per unit volume of at least the one type of micro-beads in the mixture; and
j) comparing the number of micro-beads per unit volume of the one type of beads in the imaging chamber with the concentration of the one type of beads in solution.

2. The method of claim 1 wherein the mixture of beads is counted by image processing logic associated with the analyzer.

3. The method of claim 1 wherein the two types of micro-beads are counted separately by image processing logic associated with the analyzer according to their different characteristics.

4. The method of claim 1 wherein one type of micro-bead is a fluorescent micro-bead.

5. The method of claim 1 wherein the providing provides a mixture of micro-beads of different sizes.

* * * * *